(12) United States Patent
Lazarof

(10) Patent No.: US 6,213,774 B1
(45) Date of Patent: Apr. 10, 2001

(54) PAPILLA DENTAL IMPLANT AND METHOD OF USE

(76) Inventor: Sargon Lazarof, 21237 Mulholland Dr., Woodland Hills, CA (US) 91364

( * ) Notice: Subject to any disclaimer, the term of this patent is extended or adjusted under 35 U.S.C. 154(b) by 0 days.

(21) Appl. No.: 09/287,197

(22) Filed: Apr. 6, 1999

(51) Int. Cl.[7] ................................................. A61C 8/00
(52) U.S. Cl. ................................................................ 433/173
(58) Field of Search ........................... 433/172, 173 OR, 433/174, 175, 176, 201.1

(56) References Cited

U.S. PATENT DOCUMENTS

| | | | | |
|---|---|---|---|---|
| 2,609,604 | * | 9/1952 | Sprague | 433/174 |
| 3,514,858 | * | 6/1970 | Silverman | 433/174 |
| 3,708,883 | * | 1/1973 | Flander | 433/174 |
| 4,229,169 | * | 10/1980 | Smith et al. | 433/174 |
| 4,277,238 | | 7/1981 | Katagiri | 433/201.1 |
| 4,536,158 | | 8/1985 | Bruins et al. | 433/201.1 |
| 5,462,722 | | 10/1995 | Liu et al. | 423/311 |
| 5,470,230 | * | 11/1995 | Daftary et al. | 433/173 |
| 5,499,918 | | 3/1996 | Morgan et al. | 433/173 |
| 5,749,731 | | 5/1998 | Morgan et al. | 433/173 |
| 5,984,681 | * | 11/1999 | Huang | 433/173 |

* cited by examiner

*Primary Examiner*—John J. Wilson
(74) *Attorney, Agent, or Firm*—Kelly Bauersfeld Lowry & Kelly, LLP

(57) ABSTRACT

A papilla dental implant used in a gum restorative system and its method of use are provided. The papilla dental implant provides a platform or anchor for receded gum tissue to regenerate. The system involves, generally, a papilla dental implant which is forcibly inserted and secured into a jawbone of a patient. The papilla dental implant includes a head and a tapered shaft extending from the head and tapering to a pointed terminus. The shaft of the papilla dental implant may include barbs, threads or multiple separable and expandable sections to more securely hold the implant in the bone. The shaft of the papilla dental implant is inserted and secured into the bone and the gum tissue is allowed to grow around the exposed head of the papilla dental implant, reducing or even eliminating voids or diastemas between the teeth.

12 Claims, 2 Drawing Sheets

PAPILLA DENTAL IMPLANT AND METHOD OF USE

BACKGROUND OF THE INVENTION

The present invention relates to restorative and cosmetic dentistry and particularly to the restoration of gum and bone between teeth using a papilla dental implant.

The natural gum profile or gum line of an individual typically covers the bottom portion of the teeth and invades the spaces between the teeth leaving small embrasure spaces in healthy teeth and gums. The gum profile may recede due to improper oral hygiene or gum diseases such as gingivitis and periodontal disease. The recession of the gums causes the interdental spaces to increase in size. This is particularly acute with gingivitis and periodontal disease as the bacteria which cause these diseases eat away at the gingiva and bone, causing large voids between the teeth where once there was bone and healthy gum tissue.

In some cases, the papilla and bone are severely damaged and the gum tissue cannot adequately heal to its natural state, even after aggressive treatment, as there is inadequate structure to support the regrowth of the gum tissue. These voids, referred to as diastema's or sometimes called black triangles, can be aesthetically unsightly, especially when located between the front teeth.

Therefore, what is needed is a device which is implantable within the gum and bone of the void between the teeth, acting as an anchor for the bone and gum tissue to grow around. The present invention fulfills this need and provides other related advantages.

SUMMARY OF THE INVENTION

The present invention resides in a gum tissue restorative system which utilizes a papilla dental implant that provides a platform or anchor for receded gum tissue to regenerate. The system comprises, generally, a papilla dental implant which is forcibly inserted and secured into a jawbone of the patient. The papilla dental implant includes a head having a base, and a shaft extending outwardly from the base of the head and tapering to a pointed terminus. The shaft of the papilla dental implant is inserted and secured into the bone, and the gum tissue is allowed to grow around the head of the papilla dental implant thereby reducing or even eliminating voids or diastemas between the teeth. The gum tissue may be cut to expose the jawbone before inserting the implant into the bone.

In one form of the invention, the papilla dental implant includes an arrow-shaped shaft which may have one or more barbs protruding therefrom. This form of the invention is generally tapped, terminus first, into the bone until the shaft and barbs are adequately secured into the bone and the head remains exposed.

In another form of the invention, the papilla dental implant includes a threaded shaft. In this form of the invention, the shaft is screwed into the bone until the shaft is submerged to a desired depth, securing the shaft in the bone and leaving the head exposed.

In yet another form of the invention, the papilla dental implant comprises a head having a collar rotatably connected to the head and a hollow body tapered shaft extending from the collar to a pointed terminus. The shaft includes multiple sections and a means for expanding the sections outwardly from the head. The means for expanding the sections outwardly include an expansion member movable relative to an inner threaded rod and slidably engaged with inner surfaces of the multiple sections. Both the inner threaded rod and the expansion member are disposed within the hollow body of the shaft. After inserting the shaft of the papilla dental implant into the bone, the head and inner threaded rod are rotated, moving the expansion member downwardly and expanding the sections outwardly to more securely hold the implant relative to the bone.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is an elevational view similar to FIG. 1, illustrating exposure of the bone and the void between the two front teeth and the insertion of the papilla implant of FIG. 2a;

DETAILED DESCRIPTION OF THE PREFERRED EMBODIMENTS

Figure 1:
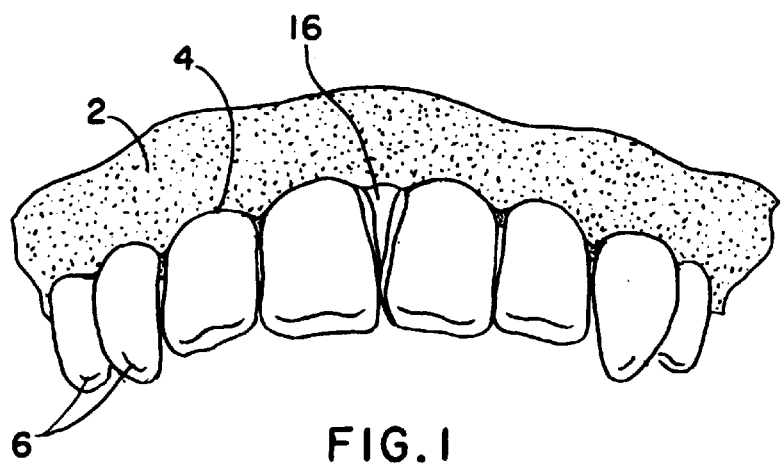
FIG. 1 is an elevational view of a row of teeth, illustrating a pronounced void between the two front teeth.

As shown in the drawings for purposes of illustration, the present invention is concerned with a gum tissue regeneration system utilizing a papilla dental implant, generally referred to by the reference numbers 10 (FIGS. 1–4), 12 (FIG. 5) and 14 (FIGS. 6 and 7), and its method of use. As illustrated in FIG. 1, patients having poor oral hygiene or gum diseases such as gingivitis or periodontal disease oftentimes lose bone structure and gum tissue 2. This loss of gum tissue 2 causes the gum line 4 to recede from the teeth 6, creating black visible voids between the teeth known as diastemas 16. By placing an object which acts as an anchor or platform protruding from the gum line 4, the gum tissue 2 is able to regenerate and grow around this object which reduces or even eliminates the diastema 16.

Figures 2A, 2B:
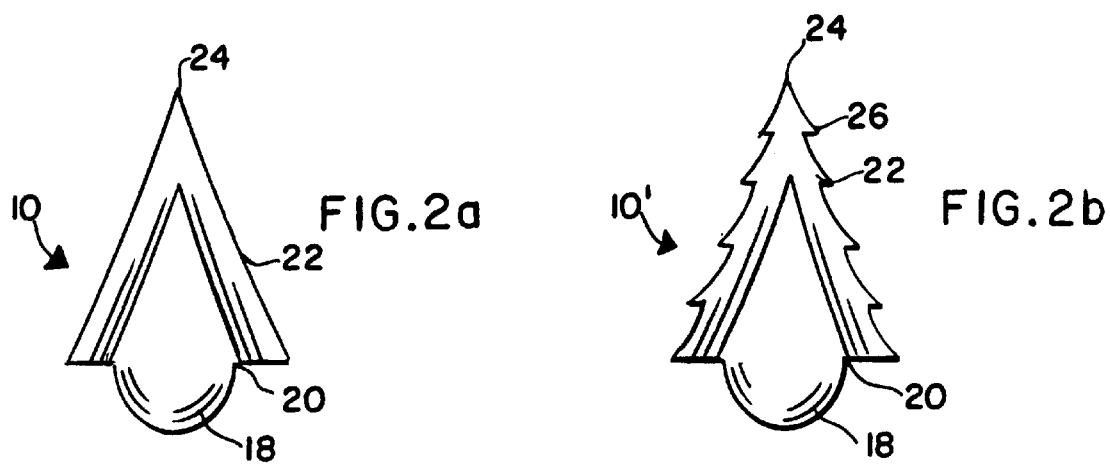
FIG. 2a is a front elevational view of a papilla dental implant embodying the invention and having an arrow-shaped shaft.
FIG. 2b is a front elevational view of the papilla dental implant similar to that shown in FIG. 2a, having barbs protruding from the shaft.
Figure 3:
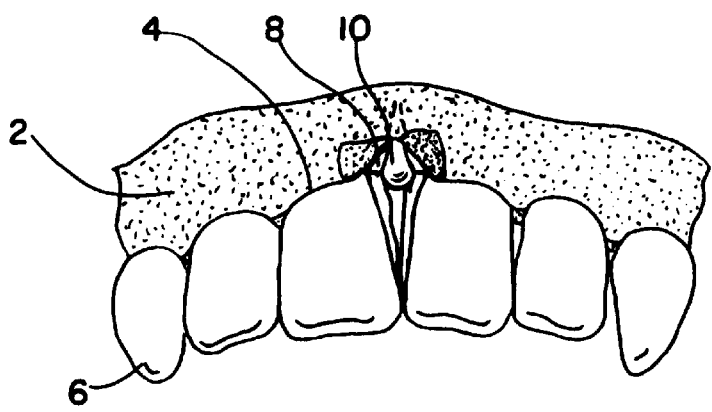
Figure 4:
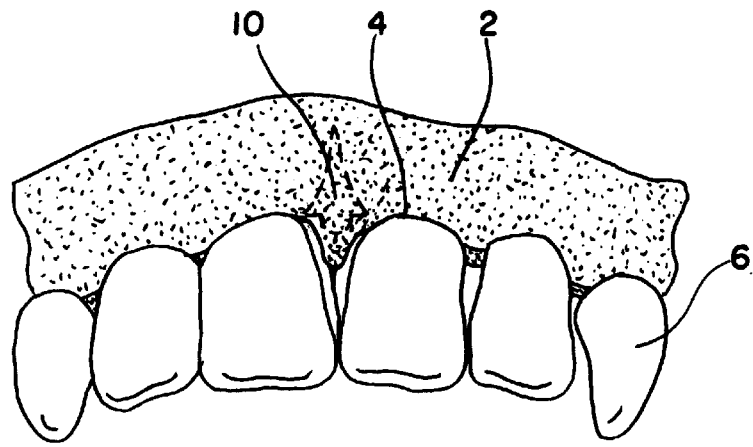
FIG. 4 is an elevational view similar to FIG. 3, illustrating the gum tissue regenerated around the implanted papilla dental implant.

In accordance with the invention and as illustrated in FIG. 2a, the papilla dental implant 10 comprises, generally, a head 18 having a base 20 and a tapered shaft 22 extending outwardly from the base 20 of the head 18 to a pointed terminus 24. A modification of this embodiment, illustrated in FIG. 2b, further includes barbs 26 formed integrally with the shaft 22 which protrude outwardly from the shaft 22 in order to more securely hold the implant 10' in the bone 8. The gum 2 may be cut to expose the bone 8, as illustrated in FIG. 3, and the pointed terminus 24 placed on the bone 8 and the shaft 22 forcibly inserted into the bone 8. As illustrated in FIG. 3, the shaft 22 is forced into the bone 8 until it is adequately secured, and the head 18 left exposed and protruding from the existing gum line 4. The implant 10 remains in place and the gum tissue 2 is allowed to regenerate and grow around the head 18 of the implant 10 filling the diastema 16 with gum tissue 2, as illustrated in FIG. 4.

Figure 5:
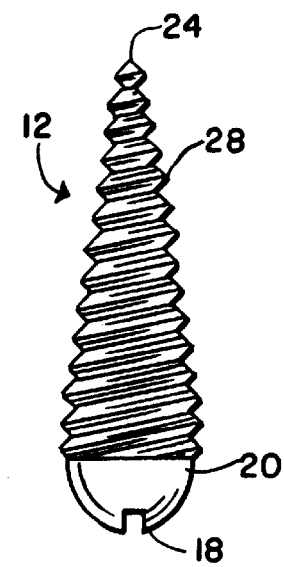
FIG. 5 is an elevational view of a papilla dental implant having a threaded shaft.

Another embodiment of the present invention is illustrated in FIG. 5. In this embodiment, the papilla dental implant 12 includes a threaded shaft 28 extending outwardly from the base 20 of the head 18 and also having a pointed terminus 24. The implant 12 is inserted into the bone 8 of the patient by forcibly screwing the threaded shaft 28 into the bone 8 until the desired depth is achieved. Once again, a portion of the implant 12, typically the head 18, remains exposed and the gum tissue 2 is allowed to regenerate around the implant 12.

Figure 6:
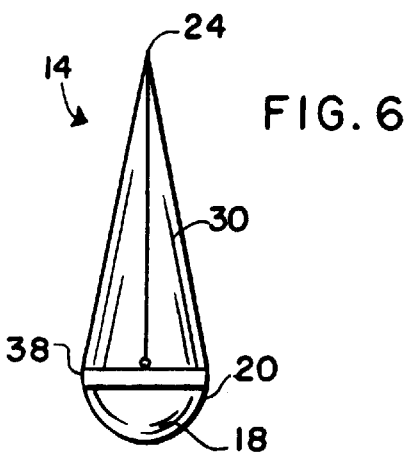
FIG. 6 is an elevational view of a papilla dental implant having multiple expanding shaft sections.
Figure 7:
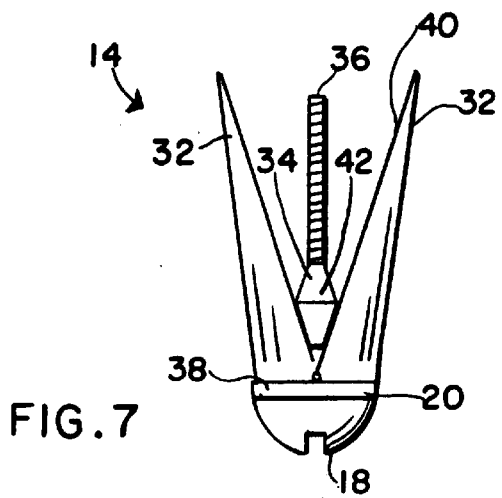
FIG. 7 is an elevational view of the papilla dental implant of FIG. 6, illustrating an expansion member moveable relative to an inner threaded rod, and the shaft sections expanded outwardly.

Yet another embodiment of the present invention is illustrated in FIGS. 6 and 7. In this embodiment, the papilla dental implant 14 comprises a hollow body shaft 30 having multiple sections 32 capable of expanding outwardly. The shaft sections 32 extend from the base 20 of the head 18 and taper to a pointed terminus 24. The means for separating and expanding the sections 32 of the shaft 30 are many, but preferably comprises the sections 32 of the hollowed shaft 30 extending upwardly from a collar 38 rotatably connected to the head 18, and an expansion member 34 movable relative to an inner threaded rod 36 but slidably engaging the interior surfaces 40 of the sections 32 as illustrated in FIG. 7.

In use, the pointed terminus 24 of the shaft 30 is placed on the bone and the shaft 30 is forcibly inserted into the bone to a desired depth. The head 18 is then rotated, causing the inner threaded rod 36 to rotate as well. The slidable collar 38 resists movement due to the forces applied by the surrounding gum tissue 2 and bone 8. The expansion member 34 typically has roughened or beveled outer surfaces 42 which are frictionally engaged, yet capable of movement, with the inner surfaces 40 of the sections 32 of the shaft 30. As the inner threaded rod 36 is rotated, the expansion member 34 moves towards the head 18 of the implant 14, expanding the sections 32 outwardly and more fully securing the implant 14 into the bone. The sections 32 may include protrusions, such as barbs or fins, for added securement to the bone. Although able to be used on all patients, this embodiment is particularly useful with patients who have experienced significant bone loss due to their gum disease as the implant 14 is able to be retained in the bone and the bone is able to regenerate around the expanded sections 32 as well as the gum tissue regenerating around the exposed head 18.

Although several embodiments have been described in detail for purposes of illustration, various modifications may be made to each without departing from the scope and spirit of the invention. Accordingly, the invention is not to be limited, except as by the appended claims.

What is claimed is:

1. A gum tissue restorative system, comprising:
   a papilla dental implant for securing to a jawbone wherein the papilla implant comprises:
   a head;
   a tapered shaft extending from the head and having a pointed terminus; and
   at least one barb formed with and protruding from a surface of the shaft;
   wherein the pointed terminus is forcibly inserted into the jawbone until the shaft is adequately secured into the jawbone leaving the head exposed.

2. A papilla dental implant, comprising:
   a head;
   a collar rotatably connected to the head;
   a tapered shaft having a pointed terminus and a hollow body and multiple sections extending from the collar of the head; and
   means for expanding the sections outwardly from the base of the head.

3. The papilla dental implant of claim 2, wherein the means for expanding the sections from the head include an expansion member moveable relative to an inner threaded rod and slidably engaged with inner surfaces of the multiple sections.

4. The papilla dental implant of claim 3, wherein the inner threaded rod and expansion member are disposed within the hollow body shaft.

5. A method of restoring gum tissue to a gap between teeth, comprising:
   providing a papilla dental implant comprising a head having a base and a tapered shaft extending from the base of the head to a pointed terminus;
   forcibly inserting and securing the shaft of the papilla dental implant into a jaw bone; and
   allowing the gum tissue to grow around the papilla dental implant.

6. The method of claim 5, including the step of cutting the gum to expose the jaw bone before inserting the papilla dental implant.

7. The method of claim 5, wherein the papilla dental implant includes at least one barb.

8. The method of claim 5, wherein the papilla dental implant further comprises a hollow shaft having multiple sections and means for expanding the sections outward.

9. The method of claim 8, wherein the means for expanding the sections from the head include an expansion member moveable relative to an inner threaded rod and slidably engaged with inner surfaces of the multiple sections.

10. The method of claim 8, including the step of expanding the sections of the shaft outwardly to more fully secure the implant into the bone.

11. The method of claim 5, wherein the step of forcibly inserting the papilla dental implant into the jaw bone comprises screwing a threaded shaft of the implant into the bone.

12. The method of claim 5, wherein the step of forcibly inserting the papilla dental implant into the jaw bone comprises tapping the head of the implant until the shaft is sufficiently secured into the bone, the head remaining exposed.

* * * * *